United States Patent [19]

Maggiulli et al.

[11] 4,025,542

[45] May 24, 1977

[54] NOVEL ETHERS, THEIR PREPARATION AND USE AS OXYDIMETHYLATING AGENTS

[75] Inventors: Cataldo Aldino Maggiulli; Donald MacArthur Burness; William Clarence Perkins, all of Rochester, N.Y.

[73] Assignee: Eastman Kodak Company, Rochester, N.Y.

[22] Filed: July 21, 1975

[21] Appl. No.: 597,950

[52] U.S. Cl. .................. 260/456 R; 260/246 B; 260/289 R; 260/306; 260/309; 260/297 R; 260/326.5 B; 260/481 R; 260/483; 260/484 R; 260/485 G; 260/513 R; 260/553 R; 260/606.5 P; 260/609 F; 260/613 R; 260/615 A

[51] Int. Cl.² ......................................... C07C 143/68

[58] Field of Search ................... 260/456 R

[56] References Cited

UNITED STATES PATENTS

| | | | |
|---|---|---|---|
| 2,581,443 | 1/1952 | Reynolds et al. | 260/456 R |
| 2,816,125 | 12/1957 | Allen et al. | 260/456 R |
| 3,200,138 | 8/1965 | Wuest | 260/456 R |
| 3,236,895 | 2/1966 | Lee et al. | 260/456 R |
| 3,737,447 | 6/1973 | Mazur et al. | 260/456 R |

OTHER PUBLICATIONS

Iliceto, Chem. Abstract, 49, 10717i–10718d, (1955).

*Primary Examiner*—James O. Thomas, Jr.
*Assistant Examiner*—Nicky Chan
*Attorney, Agent, or Firm*—Arthur H. Rosenstein

[57] ABSTRACT

A compound having the formula

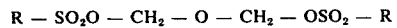

wherein R is alkyl, is prepared by reacting a compound having the formula

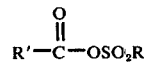

wherein R and R' are alkyl with a cyclic polyoxymethylene or a linear polyoxymethylene in a substantially humidity-free environment. The compound is useful as an oxydimethylating agent for organic compounds.

5 Claims, No Drawings

NOVEL ETHERS, THEIR PREPARATION AND USE AS OXYDIMETHYLATING AGENTS

This invention relates to a novel ether, a novel method of preparing said ether and the use of the ether as an oxydimethylating agent for organic compounds.

There are several compounds which are known in the art to be useful as alkoxyalkylating agents. These agents are compounds which can be reacted with various compounds such as mercaptans, amines, aromatic hydrocarbons, phenols and the like containing reactive groups such as hydrogen to replace the reactive group with alkoxyalkyl groups.

Thus, for example, the reaction product of dimethoxymethane with acetyl methanesulfonate is described in M. H. Karger and Y. Mazur, J. Am. Chem. Soc., 91, 5663 (1969). The resulting compound, methoxymethyl methanesulfonate, described in this reference is useful in methoxymethylating various compounds containing reactive groups.

The reactivity of methoxymethyl methanesulfonate is of a very high order, being reported by Karger and Mazur to be about $10^4$ times as reactive as the corresponding chloride and acetate. Although bifunctional analogs of the methanesulfonate until now have been unknown, they are of great potential interest, not only for the preparation of simple organic compounds but also in the preparation of polymers.

Attempts to prepare bis-sulfonates of the type described herein by various existing methods have not been successful. For example, the attempted formation of bis(p-toluenesulfonoxymethyl) ether by reaction of silver p-toluenesulfonate with a bis(halomethyl) ether led only to the p-toluenesulfonic anhydride. Furthermore, the reaction of methanesulfonyl chloride or methanesulfonic anhydride with trioxane failed to produce the dimesylate described hereinafter.

The objects of this invention are to provide (1) bifunctional compounds having great reactivity, (2) a method of preparing such compounds and (3) substances useful in the preparation of polymers, photographic hardening agents and the like. An example of their utility in hardener synthesis is their reaction with 2-mercaptoethanol to form 5-oxa-3,7-dithianonane-1,9-diol, a material described in U.S. Pat. No. 3,539,644 to Burness et al.

In accordance with the present invention, it has been found that a novel bis(organosulfonoxymethyl) ether can be prepared which can be used as an oxydimethylating agent for compounds containing reactive groups.

In one embodiment this invention comprises a compound having the formula

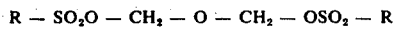
$$R - SO_2O - CH_2 - O - CH_2 - OSO_2 - R$$

wherein R is alkyl.

In another embodiment this invention comprises a novel method of preparation of bis(alkylsulfonoxymethyl) ether comprising reacting a compound having the formula

$$R'-\overset{\overset{\displaystyle O}{\|}}{C}-OSO_2-R$$

wherein R and R' are alkyl with a cyclic or linear polyoxymethylene at a temperature range of 0° to about 120° C in a substantially moisture-free atmosphere.

In still another embodiment a compound having the formula

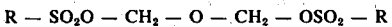
$$R - SO_2O - CH_2 - O - CH_2 - OSO_2 - R$$

wherein R is alkyl is used as an oxydimethylating agent for compounds containing reactive groups.

The novel bis(alkylsulfonoxymethyl) ether of this invention has the formula

$$R - SO_2O - CH_2 - O - CH_2 - OSO_2 - R$$

wherein R is alkyl preferably containing from 1 to 6 carbon atoms, and more preferably from 1 to 4 carbon atoms such as methyl, ethyl, propyl, butyl, and isomers thereof. The most preferred compound is that wherein R is methyl.

The above novel compounds are prepared by reacting a compound having the formula

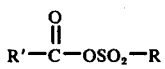
$$R'-\overset{\overset{\displaystyle O}{\|}}{C}-OSO_2-R$$

wherein R is as described above and R' is alkyl, preferably containing from 1 to 4 carbon atoms, with an ether selected from the group consisting of cyclic polyoxymethylenes such as trioxane and tetraoxane and linear polyoxymethylenes such as trioxymethylene diacetate, tetraoxymethylene diacetate, pentaoxymethylene diacetate and hexaoxymethylene diacetate having the formula

$$CH_3CO_2(CH_2O)_nCOCH_3$$

wherein n is an integer preferably from 3 to 6.

The molar ratio of compounds having the formula

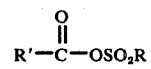
$$R'-\overset{\overset{\displaystyle O}{\|}}{C}-OSO_2R$$

such as acetyl methanesulfonate to the cyclic or linear polyoxymethylene is generally around 2:1 but can vary widely.

The reaction temperatures can vary with time of reaction. A temperature of 0° to about 120° C may be used; generally longer reaction times such as greater than 100 hours are useful at 0° C and shorter times are necessary at higher temperatures such as less than one-half hour at 100° C.

Although it is preferred to run the reaction neat, some solvents which do not react with either of the reactants may be used.

The reaction must be carried out in a substantially moisture-free environment to avoid side reactions with both the acetyl mesylate reactant and the product. In this respect, the environment preferably contains no moisture.

The novel bis(alkylsulfonoxymethyl) ether of this invention can be used as a reactant to oxydimethylate a variety of compounds generally of two classes: Class A, active hydrogen compounds preferably in the form of their alkaline metal or similar salt-like forms, such as alcohols, phenols, mercaptans, imides and active methylene compounds and B basic compounds such as are generally capable of salt formation with alkylating agents including tertiary amines, phosphines, thioethers, thiourea, amine oxides and numerous heterocyclic compounds.

Examples of compounds containing the above reactive groups include ethanol, n-butanol, chlorophenol, nitrophenol, naphthol, n-butanethiol, 2-mercaptoethanol, thiophenol, 2-mercaptoethyl acetate, α-toluenethiol, benzothiazole-2-thiol, phthalimide, diethyl malonate, ethyl acetoacetate, and the like, as well as basic compounds such as pyridine, quinoline, N-methylmorpholine, N-methylimidazole, tributylphosphine, thiolane, thiourea and pyridine-N-oxide.

Solvents useful for these reactions are generally limited due to the extreme reactivity of the dimesylate. For type A reactions tetrahydrofuran, dioxane or acetonitrile are useful and for type B reactions cyclic ethers, acetonitrile, and chlorinated solvents can be used.

Typical oxydimethylating reactions are as follows:

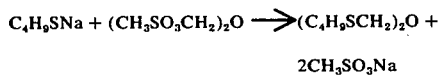

and

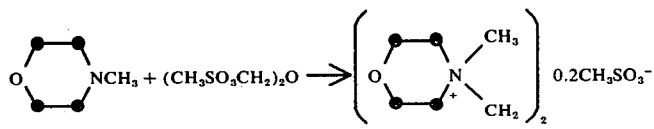

The compounds of this invention are particularly useful in oxydimethylating sodium 2-hydroxyethylmercaptide to obtain bis(vinylsulfonylmethyl) ether as described in U.S. Pat. No. 3,539,644. The oxydimethylated product is highly useful in forming hardeners for gelatino photographic materials.

The oxydimethylation reaction can be carried out, if desired, in a solvent such as cyclic ethers such as tetrahydrofuran or dioxane or acetonitrile at temperatures from 0° to about 100° C and preferably from about 0° to about 40° C.

The following examples are included for a further understanding of the invention.

EXAMPLE 1

Bis(methanesulfonoxymethyl) Ether

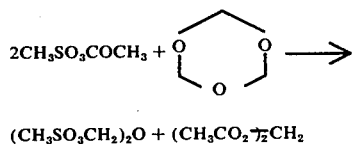

$(CH_3SO_3CH_2)_2O + (CH_3CO_2)_2CH_2$

Acetyl methanesulfonate [13.8 g, 0.1 M, prepared by the procedure described in J. Org. Chem., 36, 528 (1971)] was cooled to 5° C and 4.5 g (0.05 M) of s-trioxane was added. The mixture was stirred at 5° C for 0.5 hr. and allowed to warm gradually to 25° C. It was then heated at 80° C for 0.5 hr. and the volatiles stripped at reduced pressure. Distillation yielded 6.5 g. (60%) of bis(methanesulfonoxymethyl) ether; b.p. 122° C (pot temp.) at 7μ; m.p. 52°-53° C. Identity was established by the nmr spectrum and elementary analysis.

Anal. Calc'd. for $C_4H_{10}O_7S_2$: C, 20.4; H, 4.6; S, 27.4. Found: C, 20.3; H, 4.9; S, 27.3.

EXAMPLE 2

The acetyl methanesulfonate (285.2 g, 2.06 mole) of Example 1 was transferred by syringe to a dry-nitrogen filled flask fitted with a thermometer, magnetic stirring bar, glass adapter for nitrogen inlet and vacuum take-off. The mixed anhydride was cooled to −5° C and 92.9 g (1.03 mole) of s-trioxane was added over a 10-minute period with stirring. When the solution was complete (20 minutes), the well-stirred reaction mixture was heated to 90° C with a 0.5 mm vacuum applied when the temperature reached 35° C. Heating, with stirring, under vacuum was continued for 24 hours during which time 118.5 g (90%) of methylene diacetate was collected in a cold trap. The dark brown reaction mixture was cooled to room temperature, brought to atmospheric pressure with dry nitrogen, dissolved in 120 ml of dry tetrahydrofuran at room temperature, treated with carbon, and filtered. An additional 80 ml of dry tetrahydrofuran was used as wash solvent. The light- to medium-brown filtrate was seeded and cooled to −35° C for crystallization. The crystalline mass was broken up several times during the cold period to encourage further crystallization. The product was collected by suction filtration under dry nitrogen in a glove box, washed with cold, dry tetrahydrofuran, then with ethyl ether and dried in the funnel by drawing dry nitrogen through the funnel. A yield of 168.4 g (70%) was obtained. The bis(methanesulfonoxymethyl) ether was off-white to tan in color with a melting point in the range 52°-58° C.

EXAMPLE 3

Using the procedure of Example 2, acetyl methanesulfonate and tetroxane, in a molar ratio of 2:1, were reacted for 18-24 hours at 90° C and 0.5 mm. pressure allowing the bis(acetoxymethyl) ether to distill. The residual oil was recrystallized from a small volume of dry tetrahydrofuran to give a 67% yield of $CH_3SO_3CH_2OCH_2OSO_2CH_3$.

EXAMPLE 4

A mixture of 12.7 g of acetyl methanesulfonate and 9.15 g of trioxymethylene diacetate was prepared at 0° C and then stirred at 25° C for 20 hours. Distillation at 10μ produced 4.5 g of $CH_3SO_3CH_2OCH_2OSO_2CH_3$, b.p. 110°-115° C (pot temp.); m.p. 57°-59° C.

EXAMPLE 5

Oxydimethylation of mercaptoethanol

To a 50 ml solution of anhydrous isopropyl alcohol, containing 0.41 g (0.017 M) of sodium hydride (ether washed), was added 1.33 g (0.017 M) of 2-mercaptoethanol. The resulting suspension was stirred at 25° C for 15 minutes until a homogeneous solution was formed. A dioxane solution under $N_2$ atmosphere, containing 1.97 g (0.0084 M) of bis(methanesulfonoxymethyl) ether was then added dropwise over a 10-minute period. The reaction mixture was stirred for 1 hour at which time the insoluble materials formed were filtered off. The filtrate was concentrated to dryness and the resulting residue extracted with ethyl acetate. The extracts were evaporated to give 1.5 g (91%) of 5-oxa-3,7-dithianonane-1,9-diol, the nmr of which corresponded to that prepared from bis(chloromethyl) ether (see U.S. Pat. No. 3,539,644).

EXAMPLE 6

The procedure of Example 5 was repeated with the exception that n-butanethiol was the material oxydimethylated. The resulting product was an 85% yield of bis(butylthiomethyl) ether.

EXAMPLE 7

Oxydimethylation of N-methylmorpholine

To a solution of N-methylmorpholine in acetonitrile was added a 0.5-molar equivalent of crude $CH_3SO_3CH_2OCH_2OSO_2CH_3$. The oil which separated was added, in turn, to an aqueous solution of sodium perchlorate to produce a colorless, crystalline solid, the nmr spectrum of which confirmed the structure to be N,N'-oxydimethyl-bis(N-methylmorpholinium perchlorate).

EXAMPLE 8

Oxybis(N-methylpyridinium methanesulfonate)

A solution of a bis(methanesulfonoxymethyl) ether in 20 ml of dry acetonitrile was added dropwise to a stirred solution of 5.9 g of pyridine in 40 ml of dry acetonitrile at 25° C. The crude product began to separate almost immediately. The reaction mixture was stirred for an hour at 25° C, cooled and filtered. The crude product was recrystallized once from methanol to yield 11.7 g of the colorless crystalline salt product having a melting point of 184.5° to 186.5° C.

EXAMPLE 9

Bis(n-butoxymethyl) ether

To a solution of 0.05 mole of sodium n-butoxide and 50 ml dry n-butanol was added a solution of 0.025 mole of bis(methanesulfonoxymethyl) ether in 10 ml of dry acetonitrile at 25° C. The reaction mixture was stirred for 1 hour at 25° C and filtered. The product achieved was bis(n-butoxymethyl) ether.

EXAMPLE 10

Bis(ethanesulfonoxymethyl) ether

A sample of 64.0 g of acetyl ethanesulfonate was cooled to −10° C under dry nitrogen and 18.9 g of trioxane was added with stirring over a 15 min. period with the temperature kept below −5° C. When all of the trioxane had dissolved, the solution was allowed to warm to 10° C and a vacuum of 0.5 mm was applied. The reaction was stirred under vacuum for 18 hrs. at 80° C, cooled to room temperature and the crude product extracted with four 50 ml portions of dry ethyl ether under nitrogen in a glove box. The residue was distilled to give colorless bis(ethanesulfonoxymethyl) ether boiling at 120°–123° C (8μ), and having a refractive index $\eta_D^{24}$ 1.4551.

This invention has been described in detail with particular reference to certain embodiments thereof, but it will be understood that variations and modifications can be effected within the spirit and scope of the invention.

What is claimed is:

1. A compound having the formula:

$$R - SO_2O - CH_2 - O - CH_2 - OSO_2 - R$$

wherein R is alkyl having from 1 to 6 carbon atoms.

2. The compound of claim 1 wherein R is methyl.

3. A method of preparing a compound of claim 1 which comprises reacting a compound having the formula $$\underset{\underset{\text{R}'-\text{C}-\text{OSO}_2\text{R}}{\|}}{\text{O}}$$

wherein R' and R are independently alkyl having from 1 to 6 carbon atoms with an ether selected from the group consisting of trioxane, tetraoxane and linear polyoxymethylenes having the formla $$CH_3CO_2(CH_2O)_nCOCH_3$$

wherein n is an integer from 3 to 6 at a temperature range from about 0° to about 120° C in a substantially moisture-free environment.

4. The method of claim 3 wherein R is methyl.
5. The method of claim 3 wherein R' is methyl.

* * * * *